United States Patent
Hirano

(10) Patent No.: US 8,557,181 B2
(45) Date of Patent: Oct. 15, 2013

(54) AUTOMATIC ANALYZING DEVICE

(75) Inventor: Masaaki Hirano, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/003,337

(22) PCT Filed: Jul. 27, 2009

(86) PCT No.: PCT/JP2009/063357
§ 371 (c)(1),
(2), (4) Date: Jan. 10, 2011

(87) PCT Pub. No.: WO2010/013680
PCT Pub. Date: Feb. 4, 2010

(65) Prior Publication Data
US 2011/0104007 A1    May 5, 2011

(30) Foreign Application Priority Data

Jul. 31, 2008 (JP) .................................. 2008-197163

(51) Int. Cl.
*G01N 35/02* (2006.01)
*B01F 7/16* (2006.01)

(52) U.S. Cl.
USPC .................. 422/67; 422/63; 422/64; 436/43; 436/47; 366/255; 366/258; 366/332

(58) Field of Classification Search
None
See application file for complete search history.

(56) References Cited

U.S. PATENT DOCUMENTS

| | | | |
|---|---|---|---|
| 4,451,433 A | | 5/1984 | Yamashita et al. |
| 2007/0264156 A1 * | | 11/2007 | Yamakawa et al. ............. 422/63 |

FOREIGN PATENT DOCUMENTS

| | | | |
|---|---|---|---|
| JP | 5-27656 U | | 4/1993 |
| JP | 08-075752 | * | 3/1996 |
| JP | 8-75752 A | | 3/1996 |
| JP | 09-145718 | * | 6/1997 |
| JP | 10-62430 A | | 3/1998 |
| JP | 2005-291730 | * | 10/2005 |
| JP | 2005-291730 A | | 10/2005 |
| JP | 2007-330847 A | | 12/2007 |

* cited by examiner

*Primary Examiner* — P. Kathryn Wright
(74) *Attorney, Agent, or Firm* — Mattingly & Malur, PC

(57) ABSTRACT

A reaction solution is mixed in a short period of time with excellent stirring efficiency. During the stirring of the reaction solution, a rotation motor drives a stirring rod and a vertical motor moves the stirring rod in a vertically reciprocating manner in the reaction solution.

3 Claims, 10 Drawing Sheets

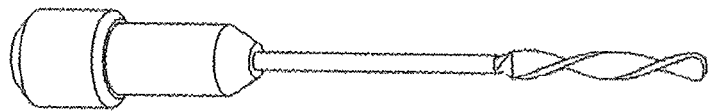
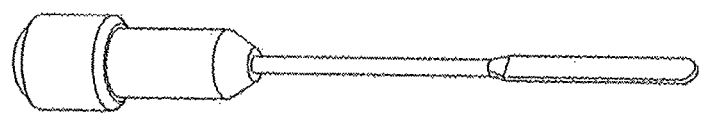
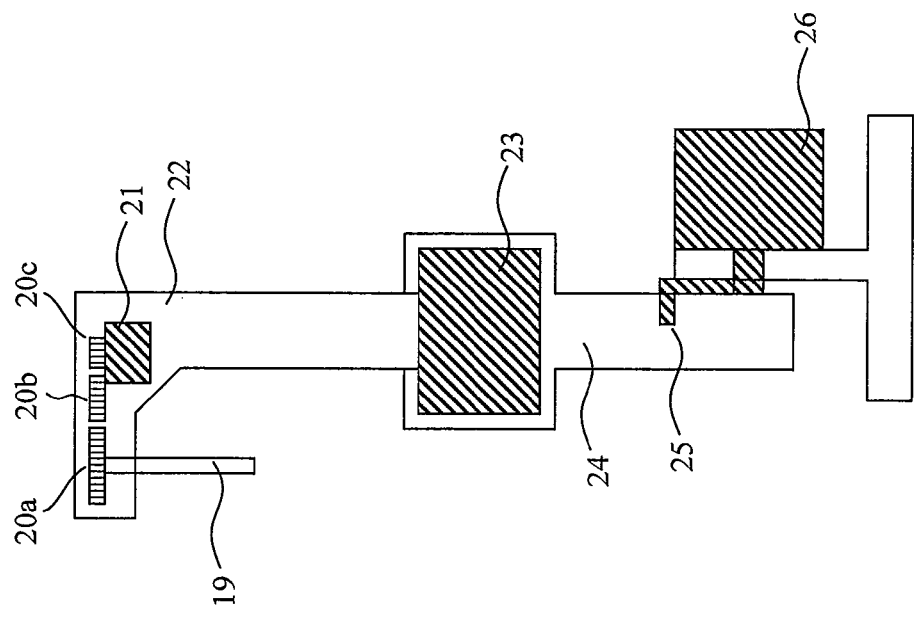

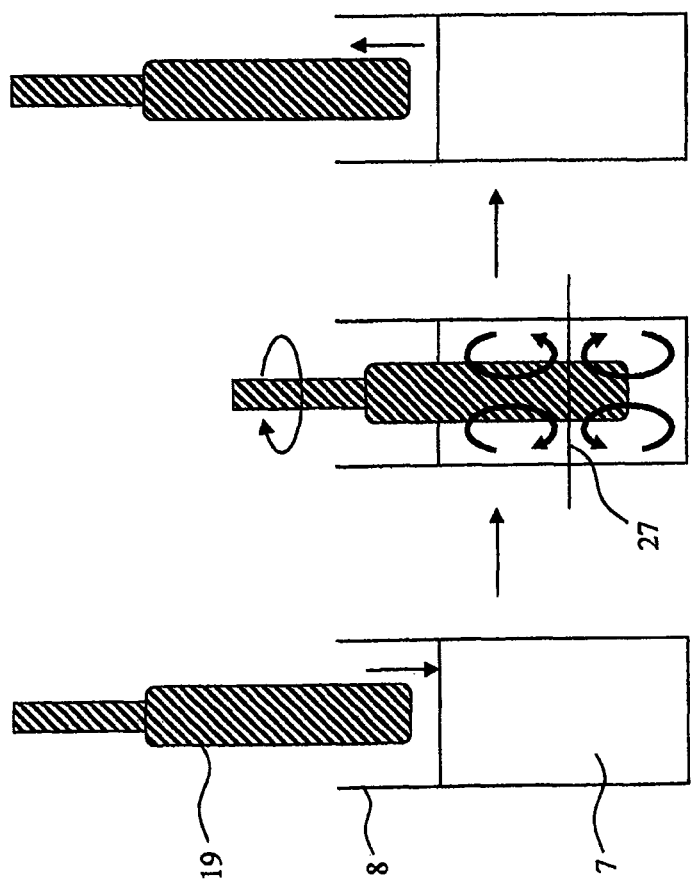

Cell A (Width 2.5mm, length 5.0mm)

| Volume (uL) | Height (mm) | 0% glycerin (Number of layers) | 20% glycerin (Number of layers) | 40% glycerin (Number of layers) |
|---|---|---|---|---|
| 50 | 4.0 | 2 | 2 | 2 |
| 60 | 4.8 | 2 | 2 | 2 |
| 70 | 5.6 | 2 | 2 | 2 |
| 80 | 6.4 | 2 | 2 | 2 |
| 90 | 7.2 | 2 | 2 | 2 |
| 100 | 8.0 | 2 | 2 | 3 |
| 110 | 8.8 | 2 | 3 | 3 |
| 120 | 9.6 | 2 | 3 | 3 |
| 130 | 10.4 | 2 | 3 | 3 |

Cell B (Width 2.5mm, length 3.0mm)

| Volume (uL) | Height (mm) | 0% glycerin (Number of layers) | 20% glycerin (Number of layers) | 40% glycerin (Number of layers) |
|---|---|---|---|---|
| 30 | 4.0 | 2 | 2 | 2 |
| 36 | 4.8 | 2 | 2 | 2 |
| 42 | 5.6 | 2 | 2 | 2 |
| 48 | 6.4 | 2 | 2 | 3 |
| 54 | 7.2 | 3 | 3 | 3 |
| 60 | 8.0 | 3 | 3 | 3 |
| 66 | 8.8 | 3 | 3 | 4 |
| 72 | 9.6 | 4 | 4 | 4 |
| 78 | 10.4 | 4 | 4 | 4 |

FIG. 7
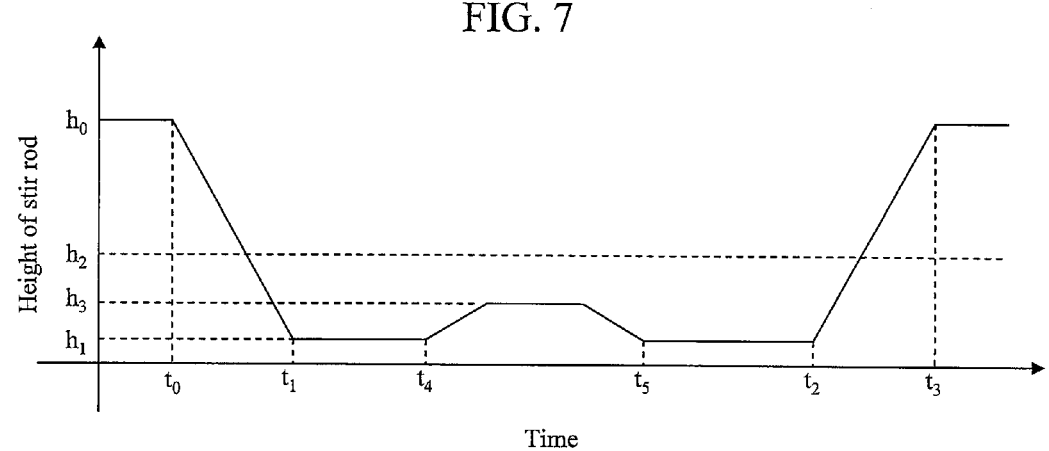
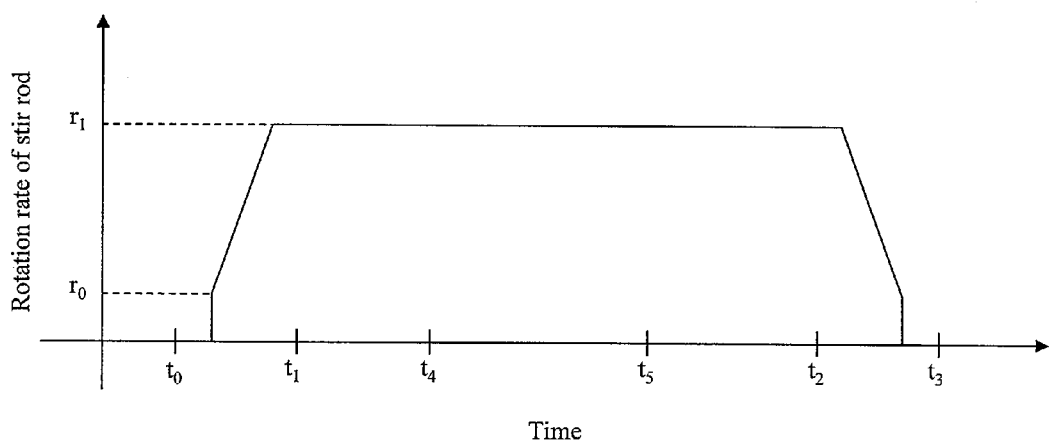

FIG. 10

| Test item | Input information | | | Reagent information | | | | Distance stir condition | | | |
|---|---|---|---|---|---|---|---|---|---|---|---|
| | Volume | | | Reagent 1 | | Reagent 2 | | Reagent 1 | | Reagent 2 | |
| | Sample | Reagent 1 | Reagent 2 | Type | Viscosity | Type | Viscosity | Move/Stay | Move distance | Move/Stay | Move distance |
| A | 2.0uL | 50uL | 50uL | A1 | 1.11mPa·s | A2 | 1.05mPa·s | Stay | — | Move | 1.0mm |
| B | 1.5uL | 60uL | 20uL | B1 | 1.02mPa·s | B2 | 0.94mPa·s | Stay | — | Stay | — |
| C | 3.0uL | 100uL | 25uL | C1 | 2.45mPa·s | C2 | 1.45mPa·s | Move | 1.0mm | Move | 2.0mm |
| D | 5.0uL | 90uL | 30uL | D1 | 1.08mPa·s | D2 | | | | | |

AUTOMATIC ANALYZING DEVICE

TECHNICAL FIELD

The present invention relates to an automatic analyzing device, and to an automatic analyzing device including a stirring mechanism for mixing a reagent, a reaction solution, and the like which are injected into a container.

BACKGROUND ART

A biochemical automatic analyzing device is known which performs biochemical analysis on a sample, such as blood, urine, or stool, by injecting the sample and a reagent into a transparent measurement container called a sample cell to react them with each other, and then optically measuring the coloration due to the reaction of the reaction solution including the sample and the reagent (refer to Patent Document 1, for example).

In this regard, after both the reagent and the sample are injected into the sample cell, the reagent and the sample are stirred in the sample cell in order to react with each other favorably and uniformly. For a biochemical automatic analyzing device, a stirring mechanism which mixes a reaction solution in a short period of time is demanded in terms of improvement in throughput. Further, in terms of reduction in the consumption volume of reagent, there is a demand for a stirring mechanism that mixes a reaction solution in a minute sample cell with which a small volume of reaction solution can be analyzed.

Patent Document 2 proposes a method of causing a stirring rod to perform a rotational movement and a reciprocal rectilinear movement in a horizontal direction at the same time for efficient stirring in a short period of time. However, analysis has to be performed with a narrow sample cell in order to handle a smaller volume of reaction solution. This requires the stirring to be performed with a limited horizontal movement.

CITATION LIST

Patent Document

Patent Document 1: U.S. Pat. No. 4,451,433
Patent Document 2: JP 10-62430 A

DISCLOSURE OF THE INVENTION

Problems to be Solved by the Invention

In a stirring mechanism that involves the rotation of a stirring rod, a phenomenon is recognized in which the flow of a solution is vertically separated into multiple layers once the solution reaches its steady state. It has been found out as a result of research that the number of layers formed by separation and the rate of propagation of a substance between the layers affect the uniformity of a stirred reaction solution. Since the rate of propagation of a substance between layers is lower than the rate of propagation of a substance within each layer, the uniformity of a reaction solution decreases with a larger number of layers formed by separation. Further, the number of layers formed by separation tends to increase in a case where a sample cell is narrow, where the volume of reaction solution is large, and where the viscosity of the reaction solution in the sample cell is high. In the field of biochemistry, various volumes of reagents with various properties are used. Accordingly, it is difficult to control the number of layers formed by separation, and is particularly difficult to make a solution uniform by stirring the solution in a short period of time in a minute sample cell suited to a small volume of reaction solution.

Means for Solving the Problems

In order to solve the above problems, according to the present invention, a stirring rod is rotated and vertically reciprocated at the same time to efficiently mix a sample and a reagent or a reaction solution to be stirred. By vertically reciprocating a stirring rod during a stirring operation of rotating the stirring rod in a reaction solution, a boundary surface between layers of flow generated in the steady state disappears and the rate of propagation of a substance increases, thus enabling efficient mixing.

Effects of the Invention

In the present invention, performing a rotational movement and a vertical reciprocating movement at the same time scrambles the flow vertically separated into multiple layers in the steady state and thereby enables efficient propagation of a substance between the layers, and thus improvement of the stirring efficiency. The present invention is an advantageous means especially for the case of stirring in a minute sample cell in a short period of time.

BRIEF DESCRIPTION OF THE DRAWINGS

FIGS. 2A to 2C are views showing an example of a configuration of a stirring unit.

FIGS. 3A to 3C are views showing a conventional stirring process.

FIG. 7 is a time chart showing a relation between the height of and the rotation rate of a stirring rod in the stirring process of the present invention.

FIG. 10 is a diagram showing associations between test-request input information and stirring conditions.

MODES FOR CARRYING OUT THE INVENTION

Embodiments of the present invention will be described in detail below with reference to the drawings.

First Embodiment

Figure 1:
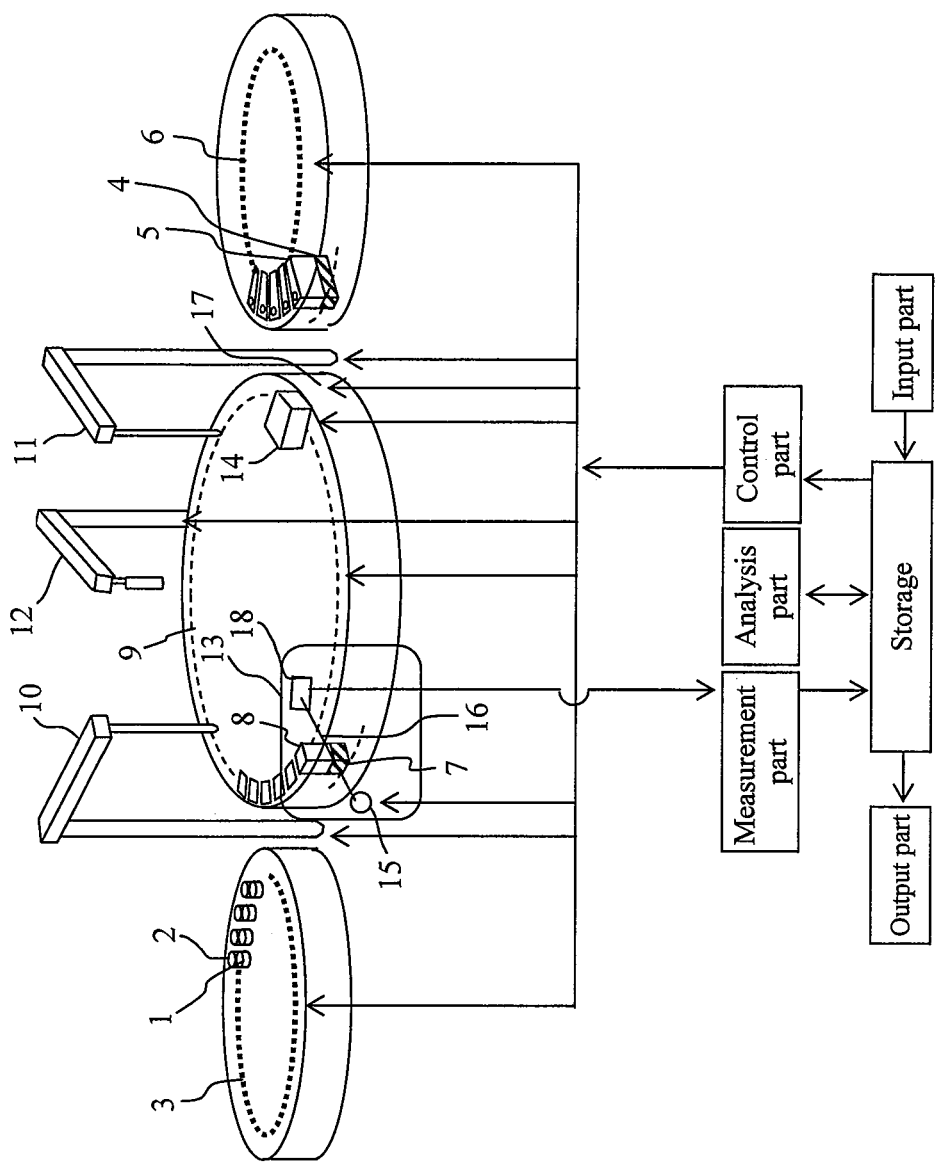
FIG. 1 is a diagram showing an example of a configuration of an automatic analyzing device.

FIG. 1 shows an example of an overall configuration of an automatic analyzing device according to the present invention. Multiple sample cups 2 each housing therein a sample 1 are arranged in a sample disk 3. Multiple reagent cups 5 each housing therein a reagent 4 are arranged in a reagent disk 6. Multiple sample cells 8 are arranged in a cell disk 9. Each sample cell 8 is used to mix the sample 1 with the reagent 4 to make a reaction solution 7. A sample pipetting mechanism 10 is capable of moving a predetermined volume of sample 1 from the inside of one of the sample cups 2 to the inside of one of the sample cells 8. A reagent pipetting mechanism 11 is capable of moving a predetermined volume of reagent 4 from the inside of one of the reagent cups 5 to the inside of one of the sample cells 8. A stirring unit 12, a measurement unit 13, and a cleaning unit 14 are arranged around the cell disk 9. The stirring unit 12 stirs and mixes the sample 1 with the reagent 4 in each sample cell 8. The measurement unit 13 performs optical measurement on the reaction solutions. The cleaning unit 14 cleans the sample cells 8. The measurement unit 13 includes a light source 15 and a light receiving element 18. The light source 15 irradiates the reaction solution 7 with light. The light receiving element 8 receives light 16 obtained by the irradiation of the reaction solution 7 with light. The sample cells 8 arranged in the cell disk 9 and the reaction solutions 7 in the cells are kept at a predetermined temperature by an constant temperature fluid 17 held in a thermostatic chamber. The automatic analyzing device also includes: a control part which controls parts of the device; a data storage part which stores therein various data; an input part through which required data can be inputted from the outside; a measurement part which calculates the absorbance of light from the amount of light received at the light receiving element 18; an analysis part which finds the amounts of ingredients from the absorbance; and an output part which is capable of displaying data and outputting the data to the outside.

The analysis of the amount of a certain ingredient in the sample 1 is conducted with the following procedure. First, the sample pipetting mechanism 10 pipettes a predetermined volume of sample 1 contained in one of the sample cups 2 into one of the sample cells 8. Next, the reagent pipetting mechanism 11 pipettes a predetermined volume of reagent 4 contained in one of the reagent cups 5 into the sample cell 8. Subsequently, the stirring unit 12 stirs the sample 1 and the reagent 4 in the sample cell 8 to make the reaction solution 7. If necessary, the reagent pipetting mechanism 11 additionally pipettes multiple reagents 4 into the sample cell 8. In the pipetting, the sample disk 3, the reagent disk 6, and the cell disk 9 are rotated to move the sample cup 2, the reagent cup 5, and the sample cell 8 to predetermined positions, respectively. After the reaction, the cleaning unit 14 cleans the inside of the sample cell 8 for the next analysis. The measurement unit 13 and the measurement part measure the absorbance of the reaction solution 7, and the absorbance data is stored in the data storage part. The analysis part is capable of analyzing the amount of the ingredient from the stored absorbance data on the basis of calibration curve data and the Lambert-Beer law. Data required for the control of each part and the analysis is inputted into the data storage part through the input part. The various data and analysis results are displayed and outputted by the output part.

FIG. 2A shows an example of a configuration of the stirring unit 12. The stirring unit 12 of this example includes: a stirring rod 19; a rotation motor 21 which is coupled to the stirring rod 19 through gears 20a, 20b, and 20c; a first support member 22 which supports the rotation motor 21; a horizontal movement motor 23 which is coupled to the first support member; a second support member 24 which supports the horizontal movement motor 23; and a vertical motor 26 which is coupled to the second support member 24 through a crank 25. Further, general shapes of the stirring rod 19 include a flat-plate shape as shown as an enlarged view in FIG. 2B and a screw shape as shown as an enlarged view in FIG. 2C. The present invention is advantageous for the stirring rod of any of these shapes.

To clarify a difference between a stirring process according to the present invention and a conventional stirring process, the conventional stirring process will be described first. The stirring unit 12 conventionally stirs a reaction solution 7 with the following procedure. First, the horizontal movement motor 23 is driven to move the stirring rod 19 to a position above one of the sample cells 8. Next, the vertical motor 26 is driven to insert the stirring rod 19 into the reaction solution 7 in the sample cell 8. Subsequently, the rotation motor 21 is driven to rotate the stirring rod 19 in the reaction solution 7, thereby performing the stirring operation. Thereafter, the vertical motor 26 is driven to pull out the stirring rod 19 to the position above the sample cell 8. The procedure described above is the process of stirring the reaction solution 7 by the stirring unit 12, and a process of cleaning the stirring rod 19 continues after this process. In the process of cleaning the stirring rod, the horizontal movement motor 23 is driven to move the stirring rod 19 to a position above a cleaning tank in the cleaning unit 14. Next, the vertical motor 26 is driven to insert the stirring rod 19 into the cleaning tank. Subsequently, the rotation motor 21 is driven to rotate the stirring rod 19 inside the cleaning tank, thereby performing the cleaning operation. Thereafter, the vertical motor 26 is driven to pull out the stirring rod 19 to the position above the cleaning tank.

Figure 4:
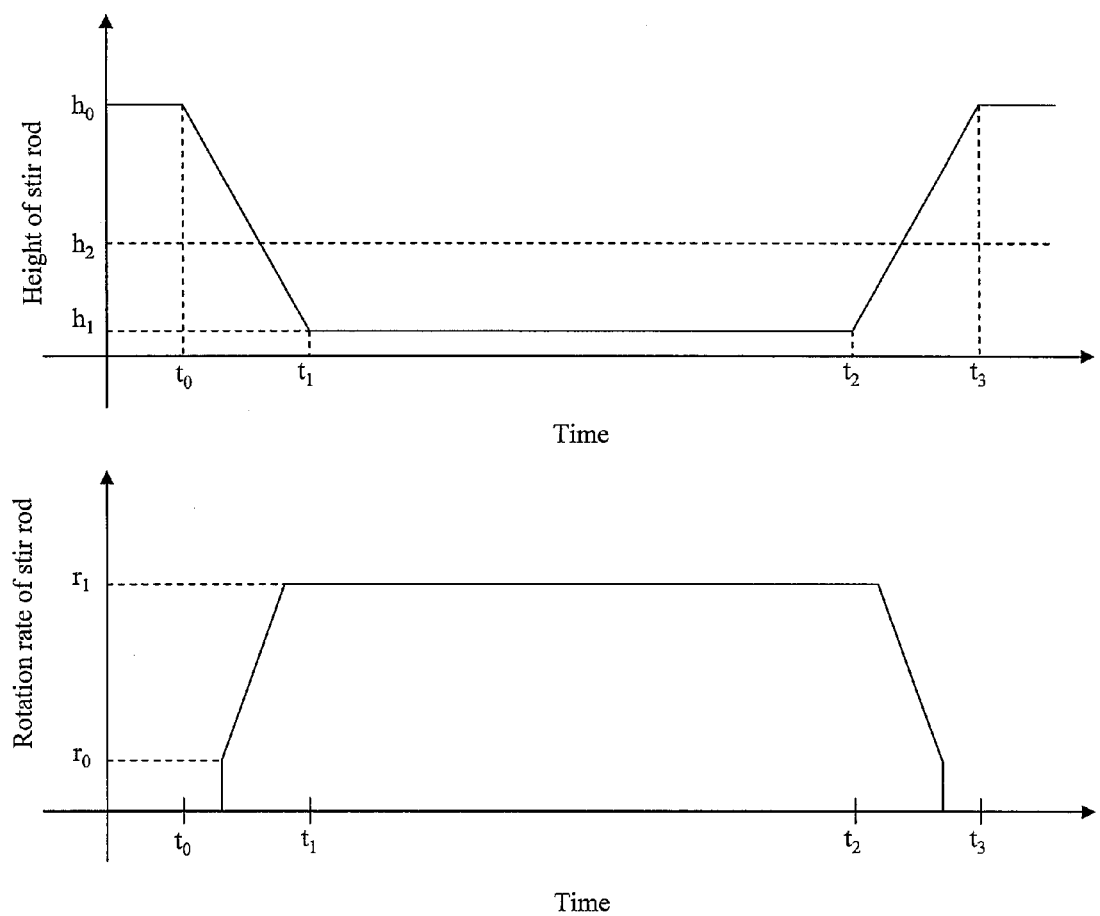
FIG. 4 is a time chart showing a relation between the height of and the rotation rate of a stirring rod in the conventional stirring process.

FIGS. 3A to 3C are schematic views showing a conventional stirring process. FIG. 4 is a time chart showing a relation between the height of a bottom end of the stirring rod 19 and the rotation rate thereof in the conventional stirring process. FIG. 3A shows the step of causing the vertical motor 26 to insert the stirring rod 19 into the reaction solution 7 in the sample cell 8. This process corresponds to time $t_0$ to time $t_1$ in FIG. 4. The stirring rod 19 descends from a height $h_0$ to a height $h_1$, and accelerates its rotation rate from $r_0$ of a stopped state to $r_1$. $h_2$ indicates the height of the reaction solution 7 and varies depending on the volume of the solution. FIG. 3B shows the step of causing the rotation motor 21 to rotate the stirring rod 19 in the reaction solution 7 to stir the solution. This process corresponds to the time $t_1$ to time $t_2$ in FIG. 4. The stirring rod 19 is kept at a height of $h_1$ and at a rotation rate of $r_1$. FIG. 3C shows the step of pulling out the stirring rod 19 to a position above the sample cell 8. This process corresponds to the time $t_2$ to time $t_3$ in FIG. 4. The stirring rod 19 ascends from the height $h_1$ to the height $h_0$, and decelerates its rotation rate from $r_1$ to $r_0$ to stop.

Here, if the stirring rod 19 is inserted into or pulled out from the reaction solution 7 while rotating at a high speed during the time $t_0$ to the time $t_1$ or during the time $t_2$ to the time $t_3$, the reaction solution 7 may splash on the surface of the solution and attach to a wall surface of the sample cell 8, thus affecting the analysis accuracy in some cases. Accordingly, in order to avoid the splash of the reaction solution 7, the conventional stirring process causes the stirring rod 19 to perform a vertical movement with its rotation being completely stopped or with a low rotation rate by adjusting the rotation rate when the stirring rod 19 passes the position of the height $h_2$, and to perform a rotational movement at a fixed position of the height $h_1$ during the time $t_1$ to $t_2$ after it is inserted and before it is pulled out. If the stirring rod 19 performs the rotational movement at the fixed position, the solution reaches its steady state, and a boundary surface of flow 27 is generated in the reaction solution 7 as shown in FIG. 3B. FIG. 3B shows an example where one boundary surface of flow 27 is generated. If the boundary surface of flow 27 is generated, the reaction solution 7 in the sample cell 8 is separated vertically at the boundary surface of flow 27, and independent flows are generated in the upper side and the lower side of the reaction solution, respectively.

Figures 5A, 5B, 5C:
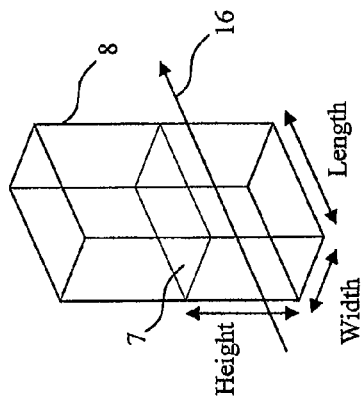
FIGS. 5A to 5C are diagrams showing the number of layers formed by separation during the stirring.

FIGS. 5A and 5B show the number of layers formed by the separation during the stirring. FIG. 5C shows a cubic diagram of the sample cell 8. In FIG. 5C, the width indicates a dimension orthogonal to a traveling direction of light for measurement 16, the length indicates a dimension parallel to the traveling direction of the light for measurement 16, and the height indicates the height of the reaction solution 7.0% to 40% glycerine was pipetted into each of two kinds of sample cells A (width: 2.5 mm, length: 5.0 mm) and B (width: 2.5 mm, length: 3.0 mm), the resultant solution in each cell was stirred by a screw-shaped stirring rod of 1.5 mm width, and the separation of the flow was observed. As a result, it was found out that the number of layers formed by the separation was two or more under any condition. In particular, the tendency of increase in the number of layers to three or more is significantly observed under the conditions where the aspect ratio of the height of the reaction solution 7 to the 2.5 mm width is 3:1 or higher. In this event, the rate of propagation of a substance in the sample 1 or the reagent 4 is lower between layers separated by the boundary surface of flow 27, than within each layer. Hence, the larger the number of boundary surfaces of flow 27, the lower the uniformity of the sample 1 and the reagent 4 in the reaction solution 7 after the stirring.

Next, a stirring process including a vertical reciprocating movement according to the first embodiment of the present invention is shown in FIGS. 6A to 6E. FIG. 7 is a time chart showing a relation between the height of the bottom end of the stirring rod 19 and the rotation rate thereof in the stirring process of the present invention.

Figure 6A:
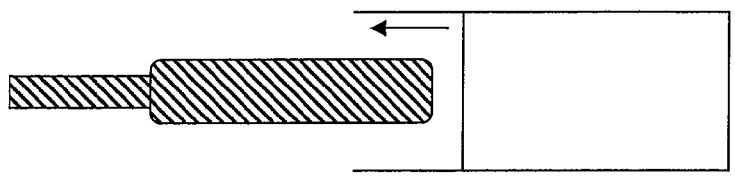
FIGS. 6A to 6E are views showing a stirring process including a vertical reciprocating movement according to the present invention.
Figure 6B:
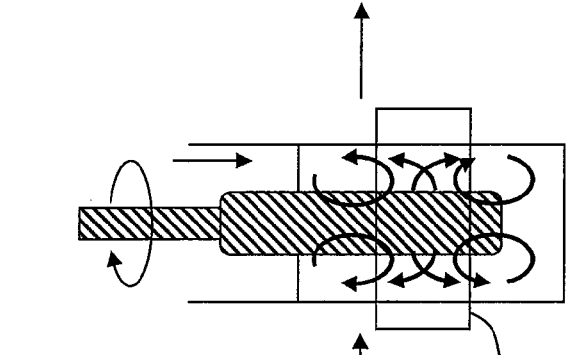
Figure 6C:
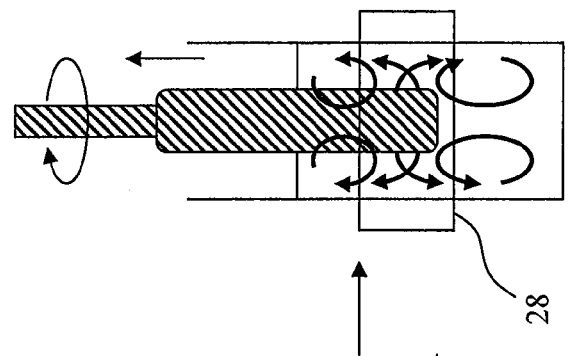
Figure 6D:
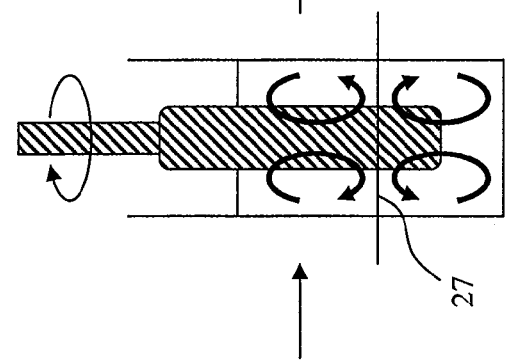
Figure 6E:
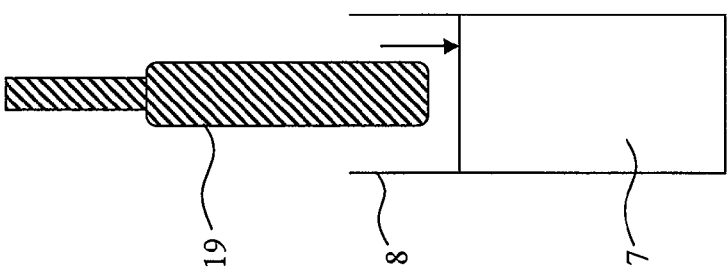

FIG. 6A shows a step of causing the vertical motor 26 to insert the stirring rod 19 into the reaction solution 7 in one of the sample cells 8. This process corresponds to time $t_0$ to time $t_1$ in FIG. 7. The stirring rod 19 descends from a height $h_0$ to a height $h_1$, and accelerates its rotation rate from $r_0$ of a stopped state to $r_1$. $h_2$ indicates the height of the reaction solution 7. FIG. 6B shows a step of causing the rotation motor 21 to rotate the stirring rod 19 at a fixed position in the reaction solution 7 to stir the solution. This process corresponds to the time $t_1$ to time $t_4$ in FIG. 7. The stirring rod 19 is kept at a height of $h_1$ and at a rotation rate of $r_1$ at which the rod achieves high-speed stable rotation. FIGS. 6C and 6D show steps of causing the vertical motor 26 to vertically reciprocate the stirring rod 19 in such a manner as to move the stirring rod upward from the fixed position $h_1$ once and downward to the fixed position again in the reaction solution 7, while causing the rotation motor 21 to rotate the stirring rod. The process shown in FIGS. 6C and 6D corresponds to the time $t_4$ to time $t_5$ in FIG. 7. The stirring rod 19 is vertically reciprocated between the height $h_1$ and a height $h_3$ with the rotation rate being kept at $r_1$. FIG. 6E shows a step of pulling out the stirring rod 19 to a position above the sample cell 8. This process corresponds to time $t_2$ to time $t_3$ in FIG. 7. The stirring rod 19 ascends from the height $h_1$ to the height $h_0$, and decelerates its rotation rate from $r_1$ to $r_0$ to stop.

Here, in FIG. 6B, a boundary surface of flow 27 is generated in the reaction solution 7 when the solution reaches its steady state. However, by rotating and vertically reciprocating the stirring rod 19 at the same time as shown in FIGS. 6C and 6D, a layer of turbulent flow 28 is formed around the area where the boundary surface of flow 27 has been generated. This increases the rate of propagation of a substance in the sample 1 or the reagent 4 between layers separated by the boundary surface of flow 27, and thus increases the uniformity of the sample 1 and the reagent 4 in the reaction solution 7 after the stirring. In this event, since the stirring rod 19 is vertically reciprocated in a state where the stirring rod 19 is immersed in the reaction solution 7, no reaction solution 7 splashes even when the stirring rod 19 rotates at a high speed.

Figure 8:
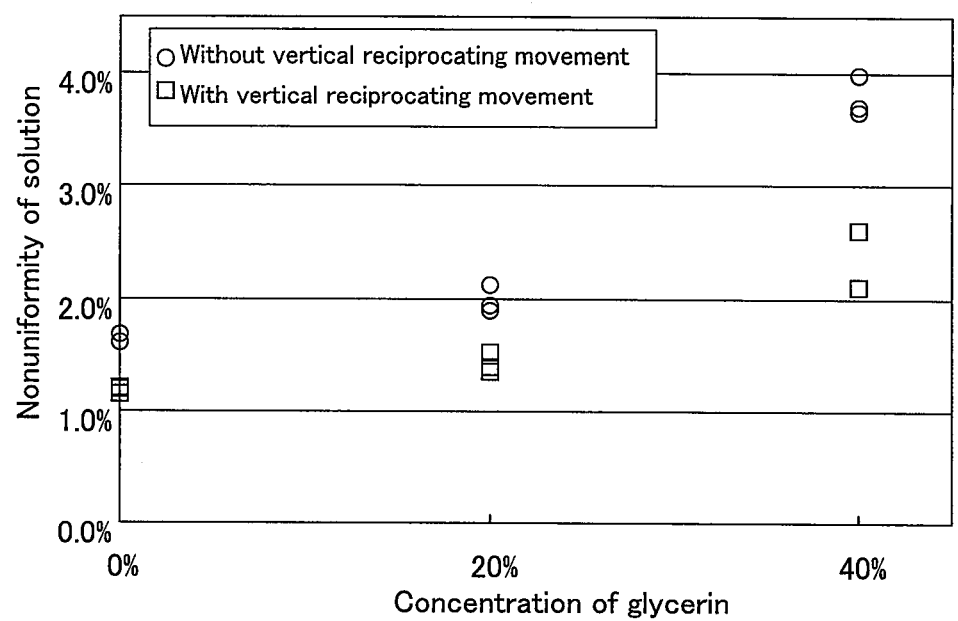
FIG. 8 is a diagram showing the nonuniformity of a glycerine solution after the stirring with/without the vertical reciprocating movement.

FIG. 8 shows the results of evaluating the nonuniformity of a glycerine solution after the stirring with/without the vertical reciprocating movement by using a simple evaluation device. A total of 130 μL of a pigment solution and a glycerine solution was pipetted into a sample cell 8 of 2.5 mm width and 5.0 mm length, and the resultant solution was stirred by a screw-shaped stirring rod 19 of 1.5 mm width. Under the condition with the vertical reciprocating movement, the stirring rod 19 in high-speed stable rotation was vertically reciprocated in such a manner that the tip of the stirring rod 19 was moved once between a position 1.0 mm above the bottom surface of the sample cell 8 and a position 2.0 mm thereabove. Under the condition without the vertical reciprocating movement, the stirring was performed under the same condition except that the tip of the stirring rod was kept at the position 1.0 mm above the bottom surface of the sample cell 8. Variation in the concentration of the solution was found from the brightness of an image obtained by photographing of the stirred solution, and thereby the nonuniformity of the solution was calculated.

As a result, as shown in FIG. 8, the uniformity of the solution with a glycerine concentration in a range of 0% to 40% was higher under the condition with the vertical reciprocating movement than under the condition without the vertical reciprocating movement. The result of FIG. 8 shows that the vertical reciprocating movement is effective in the case of using a container of 2.5 mm width. Further, the present invention is advantageous in the case of using a container of 2.5 mm dimension or smaller since the separation into layers is more likely to occur in a container of smaller dimension. Although the vertical reciprocating movement was performed in the range of 1.0 mm to 2.0 mm above the bottom surface of the sample cell 8 in this embodiment, any moving range of the vertical reciprocating movement can be set as long as the stirring rod 19 is so reliably immersed in the reaction solution 7 that no splash occurs, and does not come into contact with the bottom surface of the sample cell 8 in this range.

Second Embodiment

Figure 9:
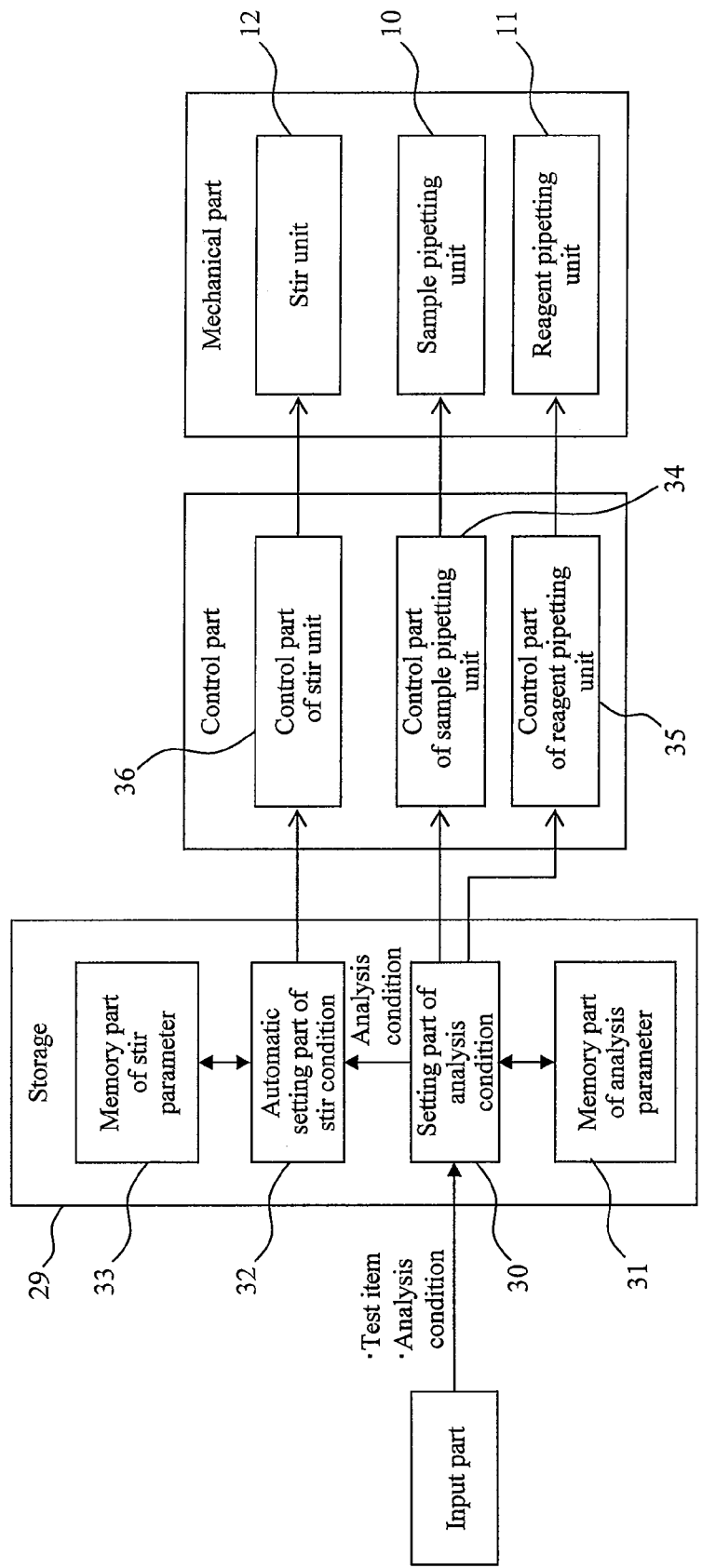
FIG. 9 is a diagram illustrating a control system for the vertical reciprocating movement according to the present invention.

FIG. 9 shows a control flow of the vertical reciprocating movement according to a second embodiment of the present invention. A requested test item and an analysis condition are inputted through the input part, and are stored in a setting part of analysis condition 30 in a storage 29. The setting part of analysis condition 30 inquires of a memory part of analysis parameter 31 about analysis parameters as needed. Next, the setting part of analysis condition 30 transmits the analysis condition to an automatic setting part of stir condition 32. Then, the automatic setting part of stir condition 32 reads, from a memory part of stir parameter 33, a stir condition associated with the volume of a reaction solution and the type of a reagent included in the analysis condition, and automatically sets parameters such as on/off of the stirring reciprocating movement and a vertical movement distance.

FIG. 10 is a diagram showing an example of associations between test-request input information and stir conditions. It is possible to previously store a database in the memory part of stir parameter 33 and determine stir conditions on the basis of input information from the input part. As shown in FIG. 10, the database associates input information, such as a test item and the volume of a sample or a reagent, with the type of reagent and stir conditions such as on/off of the vertical reciprocating movement and a reciprocating movement distance. This allows an automatic setting of stir conditions without an input of the stir conditions by the user. Thereafter, the setting part of analysis condition 30 transmits the analysis parameters to a control part of sample pipetting unit 34 and a control part of reagent pipetting unit 35, and the automatic setting part of stir condition 32 transmits the stir condition parameters to a control part of stirring unit 36. The unit control parts thereby drive the sample pipetting unit 10, the reagent pipetting unit 11, and the stirring unit 12, respectively.

REFERENCE SIGN LIST

1 sample
2 sample cup
3 sample disk
4 reagent
5 reagent cup
6 reagent disk
7 reaction solution
8 sample cell
9 cell disk
10 sample pipetting mechanism
11 reagent pipetting mechanism
12 stirring unit
13 measurement unit
14 cleaning unit
15 light source
16 light
17 constant temperature fluid
18 light receiving element
19 stirring rod
20a to 20c gear
21 rotation motor
22 first support member
23 horizontal movement motor
24 second support member
25 crank
26 vertical motor
27 boundary surface of flow
28 layer of turbulent flow
29 storage
30 setting part of analysis condition
31 memory part of analysis parameter
32 automatic setting part of stir condition
33 memory part of stir parameter
34 control part of sample pipetting unit
35 control part of reagent pipetting unit
36 control part of stirring unit

The invention claimed is:
1. An automatic analyzing device comprising:
a sample cell having a sample cell top and sample cell bottom;
a sample cell conveying part configured to convey the sample cell;
a sample injecting part configured to inject a sample into the sample cell;
a reagent injecting part configured to inject a reagent into the sample cell to fill the sample cell to a reagent solution weight;
a measurement part configured to perform optical measurement on the solution in the sample cell by irradiating the solution with light;
a stirring part configured to stir a solution in the sample cell, the stirring part includes:
a stirring rod to be inserted into the solution in the sample cell and having a stirring rod lower end;
a rotation motor configured to drive the stirring rod to rotate; and
a vertical motor configured to move the stirring rod up and down; and;
a control part configured to:
(a) accelerate a rotational speed of the rotation motor of the stirring rod from rest to a high-speed, stable rotation during a downward movement of the stirring rod by the vertical motor during a first time period from a retracted position into a fixed position in the sample solution adjacent the bottom of the sample cell,
(b) maintain the stirring rod in the fixed position in the sample solution at the high speed stable rotation for a second finite time period;
(c) move the stirring rod to move upward by the vertical motor from the fixed position to an intermediate position in which the stirring rod lower end is above the fixed position and below the reagent solution height and maintain the stirring rod at the intermediate position for a third, finite time period at the high-speed stable rotation;
(d) move the stirring rod downward from the intermediate position to the fixed position for a fourth time period while maintaining the high-speed stable rotation by the rotation motor,
(e) move the stirring rod upward by the vertical motor from the fixed position to the retracted position outside the sample solution; and
(f) decelerate the rotational speed of the stirring rod by the rotation motor from the high-speed stable rotation to rest whereby the stirring rod is not stopped completely until after the lower end of the stirring rod has been removed from the sample solution.
2. The automatic analyzing device according to claim 1, wherein at least one of a width and a length of the sample cell is 2.5 mm or smaller.
3. The automatic analyzing device of claim 1, wherein in the fixed position, the stirring rod lower end is 1.0 mm above said sample cell bottom and in the intermediate position, the stirring rod lower end is 3.0 mm above the sample cell bottom.

* * * * *